(12) United States Patent
Murata

(10) Patent No.: US 10,357,463 B2
(45) Date of Patent: *Jul. 23, 2019

(54) RIVASTIGMINE TRANSDERMAL COMPOSITIONS AND METHODS OF USING THE SAME

(71) Applicant: Teikoku Pharma USA, Inc., San Jose, CA (US)

(72) Inventor: Kensuke Murata, Tokyo (JP)

(73) Assignee: Teikoku Pharma USA, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/917,478

(22) Filed: Mar. 9, 2018

(65) Prior Publication Data

US 2018/0193285 A1  Jul. 12, 2018

Related U.S. Application Data

(63) Continuation of application No. 14/666,117, filed on Mar. 23, 2015, now Pat. No. 9,949,935.

(60) Provisional application No. 61/976,697, filed on Apr. 8, 2014.

(51) Int. Cl.
*A61K 9/70* (2006.01)
*A61K 31/27* (2006.01)

(52) U.S. Cl.
CPC ............ *A61K 9/7092* (2013.01); *A61K 9/703* (2013.01); *A61K 9/7061* (2013.01); *A61K 9/7084* (2013.01); *A61K 31/27* (2013.01)

(58) Field of Classification Search
CPC ..... A61K 9/7061; A61K 9/7092; A61K 31/27
See application file for complete search history.

(56) References Cited

U.S. PATENT DOCUMENTS

| | | | |
|---|---|---|---|
| 5,234,992 A | 8/1993 | Gyory et al. | |
| 5,240,995 A | 8/1993 | Gyory et al. | |
| 6,335,031 B1 * | 1/2002 | Asmussen | A61K 31/27 424/449 |
| 6,689,379 B1 | 2/2004 | Brachet | |
| 7,335,379 B2 | 2/2008 | Carrara et al. | |
| 8,133,510 B2 | 3/2012 | Bartholomaeus et al. | |
| 8,268,346 B2 | 9/2012 | Simes et al. | |
| 9,949,935 B2 * | 4/2018 | Murata | A61K 31/27 |
| 2007/0128263 A1 | 6/2007 | Gargiulo et al. | |
| 2007/0225379 A1 * | 9/2007 | Carrara | A61K 9/006 514/756 |
| 2010/0034838 A1 | 2/2010 | Staniforth et al. | |
| 2010/0209489 A1 * | 8/2010 | Liang | A61K 9/0004 424/450 |
| 2011/0066120 A1 | 3/2011 | Lee | |
| 2014/0083878 A1 * | 3/2014 | Tang | A61K 9/7061 206/204 |
| 2015/0209302 A1 | 7/2015 | Kawamura et al. | |

FOREIGN PATENT DOCUMENTS

| | | |
|---|---|---|
| CN | 1994290 B | 3/2011 |
| EP | 0575508 A1 | 12/1993 |
| KR | 10-2010-0079460 A | 7/2010 |
| TW | 200732001 | 9/2007 |
| WO | WO9822097 A2 | 5/1998 |
| WO | WO2012161489 A2 | 11/2012 |
| WO | WO2013047410 A1 | 4/2013 |
| WO | WO2014047191 A1 | 3/2014 |

OTHER PUBLICATIONS

Abu-Huwaij et al., Formulation and In Vitro Evaluation of Xanthan Gum or Carbopol 934-Based Mucoadhesive Patches, Loaded with Nicotine, AAPS PharmSciTech (2011), 12(1):21-27.
Ahad et al., Investigation of antihypertensive activity of carbopol valsartantransdermal gel containing 1,8-cineole, Int J Biol Macromol (2014), 64:144-149.
Carbopol Polymers Overview, The Lubrizol Corporation, 2008, 41 pages.
Carbopol 934P NF Polymer by Lubrizol, undated, 2 pages.
Carbopol 934P NF Polymer, Lubrizol, Product Specification, Issued on Jun. 14, 2007, 1 page.
Lubrizol Corporation, Polymer for Pharmaceutical Applications, Pharmaceutical Bulletin 1, May 31, 2011, pp. 1-9.
Lubrizol, Carbopol Polymer Products, retrieved from the internet on Mar. 31, 2017 at <URL: https://www.lubrizol.com/en/Life-Sciences/Products/Carbopol-Polymer-Products>, pp. 1-4.

* cited by examiner

*Primary Examiner* — Michael B. Pallay
(74) *Attorney, Agent, or Firm* — Khin K. Chin; Bret E. Field; Bozicevic, Field & Francis LLP

(57) ABSTRACT

Rivastigmine transdermal compositions are provided. Aspects of the transdermal compositions include an active agent layer which includes rivastigmine and a solubility modulator, e.g., crosslinked acrylic acid polymer. Also provided are methods of using the transdermal compositions and kits containing the transdermal compositions.

23 Claims, 9 Drawing Sheets

Formulation 3:
Lot 170-28-1 (20%RIV/2% Carbopol974P/0.1%Vit.E/10%Plastoid B/67.9% DT-2353)
Coat Weight : 18 mg/cm²

Formulation 4:
Lot 170-28-2 (20%RIV/2% Carbopol974P/0.1%Vit.E/10%Plastoid B/67.9% DT-2353)
Coat Weight : 36 mg/cm²

RIVASTIGMINE TRANSDERMAL COMPOSITIONS AND METHODS OF USING THE SAME

CROSS-REFERENCE TO RELATED APPLICATIONS

This application is a continuation of U.S. application Ser. No. 14/666,117 filed Mar. 23, 2015, which application claims priority to the filing date of U.S. Provisional Application Ser. No. 61/976,697 filed Apr. 8, 2014, pursuant to 35 U.S.C. § 119(e); the disclosure of which are herein incorporated by reference.

INTRODUCTION

Acetylcholine is an important neurotransmitter associated with memory. Deficiencies in cholinergic neurotransmission in subjects suffering from dementia (e.g., Alzheimer's disease) have led to the development of cholinesterase inhibitors as a first-line treatment for symptoms of this disease. The clinical benefits of these agents include cognitive improvements, stabilization or less than expected decline in cognition, function and behavior.

The common mechanism of action underlying cholinesterase inhibitors is an increase in available acetylcholine through inhibition of the catabolic enzyme, acetylcholinesterase. It is now recognized that cholinesterase inhibitors, including donepezil, galantamine and rivastigmine, decrease acetylcholinesterase activity in a number of brain regions in patients with Alzheimer's disease. There is also a significant correlation between acetylcholinesterase inhibition and observed cognitive improvement. As a class, the currently approved cholinesterase inhibitors (donepezil, galantamine, rivastigmine and tacrine) provide important benefits in patients with Alzheimer's disease and these drugs offer a significant advance in the management of dementia.

Rivastigmine, i.e., (S)-3-[1-(dimethylamino)ethyl]phenyl N-ethyl-N-methylcarbamate (trade name Exelon®), inhibits both acetylcholinesterase and butyrylcholinesterase. By inhibiting cholinesterase-mediated breakdown of acetylcholine, rivastigmine enhances the durability of acetylcholine in the brain, including in brain regions in which low acetylcholine levels are associated with memory problems (dementia) associated with Alzheimer's disease and Parkinson's disease.

SUMMARY

Rivastigmine transdermal compositions are provided. Aspects of the transdermal compositions include an active agent layer which includes rivastigmine and solubility modulator, e.g., a crosslinked acrylic acid polymer. Also provided are methods of using the transdermal compositions and kits containing the transdermal compositions.

DETAILED DESCRIPTION

Figure 1:
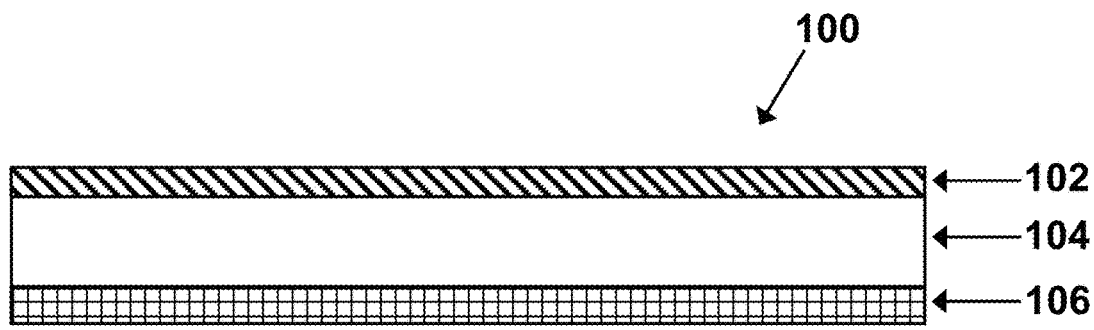
FIG. 1 shows a rivastigmine transdermal composition according to one embodiment of the present disclosure.

Rivastigmine transdermal compositions are provided. Aspects of the transdermal compositions include an active agent layer which includes rivastigmine and a solubility modulator, e.g., crosslinked acrylic acid polymer. Also provided are methods of using the transdermal compositions and kits containing the transdermal compositions.

Before the present disclosure is described in greater detail, it is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

In further describing various embodiments of the present disclosure, aspects of the transdermal compositions are reviewed first in greater detail, followed by a detailed description of embodiments of using the transdermal delivery systems and a review of kits that include the transdermal delivery systems.

Rivastigmine Transdermal Compositions

As summarized above, rivastigmine transdermal compositions are provided. The transdermal compositions include an active agent layer that includes rivastigmine and a crosslinked acrylic acid polymer. In certain aspects, the rivastigmine is present in an amount of 10% w/w or more (e.g., 20% w/w or more). The transdermal compositions, in some instances, further include a backing layer and a peelable release liner.

Transdermal compositions of the invention are formulations that are configured to transdermally deliver an active agent, specifically rivastigmine, to a subject when topically applied to a skin surface of a subject. The compositions of the invention include a rivastigmine-containing active agent layer, where the rivastigmine-containing active agent layer is formulated to provide for multi-day delivery of a therapeutically effective amount of rivastigmine to a subject when the composition is topically applied to said subject. By multi-day delivery is meant that the layer is formulated to provide a therapeutically effective amount to a subject when the composition is applied to a skin site of a subject for a period of time that is 1 day or longer, such as 2 days or longer, e.g., 3 days or longer, such as 4 days or longer, such as 5 days or longer, such as 6 days or longer, including 7 days or longer, such as 10 days or longer, and in some instances 14 days or less, such as 10 days or less. By therapeutically effective amount is meant that the compositions, when applied to a skin site of a subject during its intended time of application, e.g., within 7 days of application, provides for a systemic amount of rivastigmine that provides a desired therapeutic activity. In some embodiments, the compositions provide delivery of a target dosage of active agent that is 4.0 mg/day or greater over a one week period (i.e., 7 days or 168 hours), including 9.5 mg/day or greater over a one week period, such as 13.3 mg/day or greater over one week, wherein some instances the target dosage is 30 mg/day or less, such as 20 mg/day or less over one week.

Transdermal compositions according to certain embodiments of the present disclosure exhibit a therapeutically sufficient flux of rivastigmine over an extended period of time. A therapeutically sufficient flux of rivastigmine over an extended period of time may be defined such that the average delivery flux on the first day should not be greater than a fixed criterion from the average daily flux on the last day of wear, for example, day 1 and day 3 or day 1 and day 7. The fixed criterion can vary, ranging from a factor of 5 to a factor of 1, such as a factor of 4 to a factor of 1.25, where in some instances the fixed criterion is a factor of 3, or a factor of 2 or a factor of 1.5. The extended period of time over which substantially the flux is observed may vary, and in some instances is 24 hours or longer, such as 48 hours or longer, including 72 hours or longer, e.g., 96 hours or longer, including 120 hours or longer, such as 144 hours or longer, e.g., 168 hours or longer, including 240 hours or longer. While the actual flux may vary, in some instances (e.g., as determined using the skin permeation assay reported in the Experimental Section, below) skin permeation rates of 1 $\mu g/cm^2/hr$ or greater, such as 4 $\mu g/cm^2/hr$ or greater, e.g., 5 $\mu g/cm^2/hr$ or greater, including 6 $\mu g/cm^2/hr$ or greater are provided by the compositions, wherein in some instances the flux is 40 $\mu g/cm^2/hr$ or less, such as 20 $\mu g/cm^2/hr$ or less.

In certain aspects, the therapeutic flux ranges from 1 to 40 $\mu g/cm^2/hr$, such as from 1 to 20 $\mu g/cm^2/hr$, such as from 2 to 20 $\mu g/cm^2/hr$, such as from 2 to 15 $\mu g/cm^2/hr$, including from 5 to 15 $\mu g/cm^2/hr$, e.g., for an extended period of time (e.g., from 2 to 10 days, including 5 or more days, e.g., 7 or more days).

Transdermal compositions as described herein provide for desirable Cmin/Cmax. Cmin/Cmax refers to the minimum plasma level of rivastigmine over maximum over a wear period (e.g., 3 or more days, such as 5 or more days, including 7 or more days) and is a measure of the depletion the depletion of rivastigmine from the topical formulation over the wear period. If Cmin/Cmax is low, a conclusion can be made that the topical formulation is not retaining the drug administration during wear period, and blood concentration is continuing to decrease over the wear period. In some instances, the topical formulations provide a Cmin/Cmax of 0.4 or higher, such as 0.5 or higher where in some instances the Cmin/Cmax is 1.0 or lower, such as 0.75 or lower, e.g., 0.6 or lower.

The size (i.e., area) of the transdermal compositions may vary. In certain embodiments, the size of the composition is chosen in view of the desired transdermal flux rate of the active agent and the target dosage. For example, if the transdermal flux is 40 µg/cm$^2$/hr and the target dosage is 12 mg/day, then the transdermal composition is chosen to have an area of ranging from 5 to 15 cm$^2$. Or for example, if the transdermal flux is 20 µg/cm$^2$/hr and the target dosage is 6 mg/day, then the transdermal patch is chosen have an area ranging from 5 to 15 cm$^2$. In certain aspects, the compositions have dimensions chosen to cover an area of skin when applied to a skin site that ranges from 10 to 200 cm$^2$, such as 20 to 150 cm$^2$, including 40 to 140 cm$^2$, e.g., 60 cm$^2$. According to certain embodiments, the dimensions of the active agent layer range from 5 to 75 cm$^2$, such as from 15 to 60 cm$^2$, such as from 10 to 50 cm$^2$, including from 20 to 50 cm$^2$, e.g., 20 to 40 cm$^2$, including 35 cm$^2$.

The rivastigmine-containing active agent layer of the compositions may vary in coat weight. In some instances, the coat weight of the active agent layer ranges from 2.5 mg/cm$^2$ to 100 mg/cm$^2$, such as from 2.5 mg/cm$^2$ to 50 mg/cm$^2$, such as 5 mg/cm$^2$ to 20 mg/cm$^2$, e.g., 7.5 mg/cm$^2$ to 15 mg/cm$^2$, including 9 mg/cm$^2$ to 12 mg/cm$^2$ in coat weight. Since the difficulty and cost in manufacturing increases with thicker active agent layers and yet thicker layers allow for less depletion of drug and hence less decreasing flux during wear, in some instances a coat weight that represents a balance of these parameters is employed, e.g., a coat weight ranging from 10 to 90 mg/cm$^2$, such as 20 to 70 mg/cm$^2$, and including 25 to 50 mg/cm$^2$.

An aspect of the transdermal compositions according to certain embodiments of the present disclosure is that they are storage stable. By storage-stable is meant that the compositions may be stored for extended periods of time without significant degradation and/or significant reduction in activity of the rivastigmine. In certain embodiments, the subject compositions are stable for 6 months or longer, such as 1 year or longer, including 18 months or longer, 2 years or longer, e.g., 3 years or longer, etc., when maintained at 25° C. and 60% RH as defined in the WHO technical Report Series No. 953 (2009). In some cases, the ratio of the amount of rivastigmine in the composition to the initial amount of rivastigmine in the composition after storage at about 60° C. for at least one month is 50% or more, 60% or more, such as 70% or more, including 80% or more, or greater, including 90% or greater, 95% or greater, 98% or greater, including 99% or greater, in some instances up to 100% or greater to account for experimental error and variation in coating dispensing In some instances, the transdermal compositions are configured with as a single layer composition. By "single layer" is meant that the transdermal delivery device includes only a single layer of active agent containing matrix and does not include separate distinct layers for the pressure sensitive adhesive, transdermal active agent layer, etc. Likewise, single layer transdermal delivery devices of the present invention do not further include a separate active agent reservoirs (i.e., an active agent reservoir) separate from the pressure sensitive adhesive. As such, single layer transdermal compositions of the present invention may include in a single matrix an amount of each of the components of the transdermal compositions necessary for practicing the subject methods, as described in greater detail below. For example, in some embodiments, single layer transdermal compositions of interest include a single layer matrix of rivastigmine and an adhesive. According to some embodiments, the compositions of the present disclosure include a backing, and a rivastigmine-containing active agent layer. The composition may further include a release liner. For example, FIG. 1 illustrates a transdermal composition 100 according to an embodiment of the present disclosure, where composition 100 includes backing 102, rivastigmine-containing active agent layer 104, and release liner 106.

Figure 2:
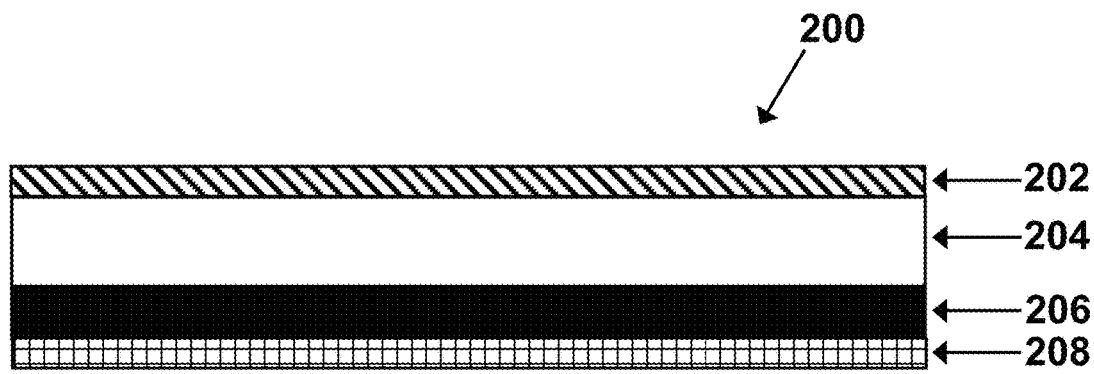
FIG. 2 shows a rivastigmine transdermal composition according to one embodiment of the present disclosure.

In certain aspects, the compositions of the present disclosure include a backing, a rivastigmine-containing active agent layer, and an adhesive layer. Such compositions may further include a release liner. For example, FIG. 2 illustrates transdermal composition 200 according to an embodiment of the present disclosure, where composition 200 includes backing 202, rivastigmine-containing active agent layer 204, skin adhesive layer 206, and release liner 208. The composition may include a membrane (not shown), e.g., between active agent layer 204 and skin adhesive layer 206, within active agent layer 204, and/or within skin adhesive layer 206. In embodiments where two layers of adhesive are in contact with each other, a porous material such as nonwoven, woven, paper, membrane, or other topically well-tolerated porous material, may be included between the adhesive layers to minimize cold flow and to provide additional mechanical strength.

Figure 3:
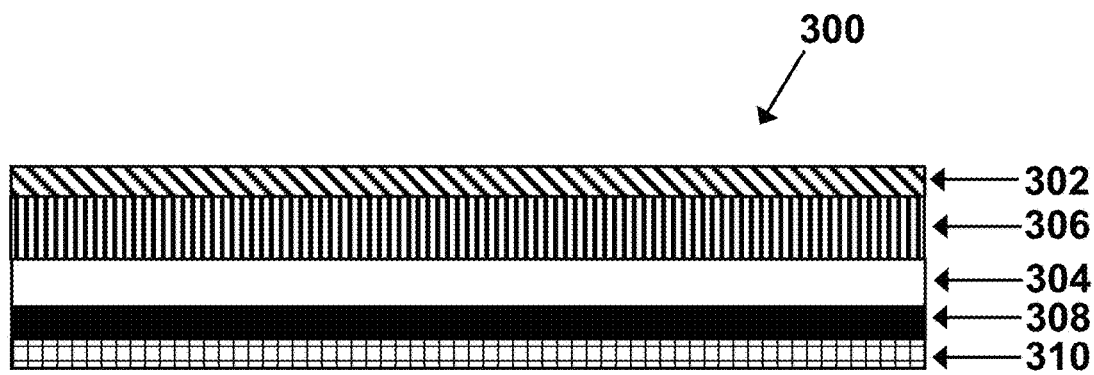
FIG. 3 shows a rivastigmine transdermal composition according to one embodiment of the present disclosure.

According to certain embodiments, the compositions of the present disclosure are three-layer compositions. In certain aspects, the three-layer compositions include a backing, a first rivastigmine-containing active agent layer which includes a crosslinked acrylic acid polymer, a second rivastigmine-containing active agent layer which may or may not include a crosslinked acrylic acid polymer, and an adhesive layer. Such compositions may further include a release liner. For example, FIG. 3 illustrates transdermal composition 300 according to an embodiment of the present disclosure, where composition 300 includes backing 302, first rivastigmine-containing active agent layer 304 which includes a crosslinked acrylic acid polymer, second rivastigmine-containing active agent layer 306 which does not include a crosslinked acrylic acid polymer, skin adhesive layer 308, and release liner 310. The composition may include a membrane (not shown), e.g., between first rivastigmine-containing active agent layer 304 and second rivastigmine-containing active agent layer 306, between second rivastigmine-containing active agent layer 306 and skin adhesive layer 308, within first rivastigmine-containing active agent layer 304, within second rivastigmine-containing active agent layer 306, and/or within skin adhesive layer 308. These layers and other components are now described in greater detail.

Transdermal compositions of the present disclosure may include two or more layers, where the composition includes a crosslinked acrylic acid polymer-containing active agent layer and a skin-adhesive layer that does not include a crosslinked acrylic acid polymer. In use, the skin-adhesive layer of such compositions is the layer that directly contacts the surface of a skin site of a subject. Because certain crosslinked acrylic acid polymers exhibit moisture-absorbing properties which may affect the flux of rivastigmine from the crosslinked acrylic acid polymer-containing active agent layer, in certain aspects, the skin adhesive layer reduces or prevents moisture uptake by the crosslinked acrylic acid polymer in the active agent layer, e.g., moisture (e.g., sweat) from the skin site of a subject to which the composition is topically applied. According to certain embodiments, the skin adhesive layer reduces or eliminates potential variability in rivastigmine flux based on differing skin moisture levels between subjects, e.g., subjects who produce skin moisture (e.g., sweat) at different rates. Accordingly, the skin-adhesive layer serves at least the dual roles of facilitating adherence of the transdermal composition to the skin site of a subject, and reducing or preventing moisture uptake by the crosslinked acrylic acid polymer in the active agent layer.

First Active Agent Layer

As summarized above, the transdermal compositions of present disclosure include a rivastigmine-containing active agent layer, e.g., present on a surface of a backing. Rivastigmine is an inhibitor of acetylcholinesterase and butyrylcholinesterase having the empirical formula $C_{14}H_{22}N_2O_2$. Rivastigmine is known chemically as (S)-3-[1-(dimethylamino)ethyl]phenyl N-ethyl-N-methylcarbamate and has the following formula:

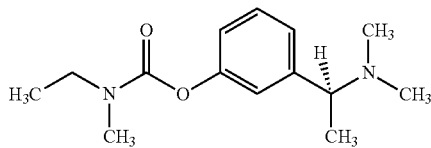 [SMILES: CCN(C)C(=O)Oc1cccc([C@H](C)N(C)C)c1]

Active agent layers of interest include rivastigmine present in an amount of from 10% to 75% w/w, such as from 15% to 50% w/w, including from 20% to 40% w/w, e.g., 30% w/w. In certain aspects, the rivastigmine is present in the active agent layer in an amount of 5% w/w or more, 10% w/w or more, 15% w/w or more, 20% w/w or more, 25% w/w or more, 30% w/w or more, 35% w/w or more, 40% w/w or more, or 45% w/w or more. According to certain embodiments, the rivastigmine is present in the active agent layer in an amount of 50% w/w or less, 45% w/w or less, 40% w/w or less, 35% w/w or less, 30% w/w or less, 25% w/w or less, 20% w/w or less, or 15% w/w or less.

The rivastigmine may be present in the active agent layer as a free base or salt. According to certain aspects, the rivastigmine is present as a salt. Rivastigmine salts of interest include, but are not limited to, rivastigmine tartrate, rivastigmine hydrochloride, etc.

In certain embodiments, e.g., to provide better skin adhesion for extended wear periods, the backing may be comprised of multiple layers. In particular, an adhesive layer that may or may not contain the active agent may be in contact with the backing. In certain cases, the backing has a larger surface area than the active agent reservoir, e.g., by 5% or more, such as 10% or more, including 15% or more. In such embodiments, an adhesive, for example a polyisobutylene-based adhesive, which can hold minimal active agent is in contact with the full surface area of the backing. Moreover, in this embodiment, a central portion of this adhesive layer with minimal active agent content may be in contact with either the active agent adhesive layer or another backing layer that separates the two adhesive layers.

As summarized above, the first active agent layer includes a solubility modulator. The solubility modulator may be a solubility enhancer. In some instances, the solubility modulator further functions as a "cold flow reducer," such that it retards, if not inhibits, the release of the active agent from the active agent layer, e.g., adhesive thereof. In some instances, the solubility modulator, e.g., enhancer, is a polymeric solubility modulator, such as a crosslinked acrylic acid polymer. The crosslinked acrylic acid polymer includes crosslinked polymers that include one or more acrylic acid monomers. In certain aspects, 10% or more, 20% or more, 30% or more, 40% or more, 50% or more, 60% or more, 70% or more, 80% or more, 90% or more, or 95% or more of the monomers of the crosslinked polymers are acrylic acid monomers. According to certain embodiments, 95% or less, 90% or less, 80% or less, 70% or less, 60% or less, 50% or less, 40% or less, 30% or less, 20% or less, or 10% or less of the monomers of the crosslinked polymers are acrylic acid monomers.

The crosslinked acrylic acid polymer may vary. In certain aspects, the crosslinked acrylic acid polymer is a copolymer that includes acrylic acid monomers and non-acrylic acid monomers in any desired proportion. In other aspects, the crosslinked acrylic acid polymer is a crosslinked acrylic acid homopolymer, in which the polymer includes acrylic acid monomers and does not include non-acrylic acid monomers. Such polymers have the general formula:

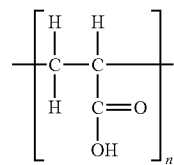

Crosslinked acrylic acid polymers of interest include carbomer polymers, which are high molecular weight, crosslinked non-linear polyacrylic acid polymers. Carbomer polymers of interest include, but are not limited to, the commercially available Carbopol® polymers (Lubrizol Corp., Wickliffe, Ohio). Carbopol® polymers that find use in the active agent layer of the compositions of the present disclosure include, e.g., Carbopol® 934P, Carbopol® 974P, Carbopol® 71G, Carbopol® 971P, Carbopol® 980, Carbopol® 981, Carbopol® 5984, Carbopol® ETD 2020, Carbopol® Ultrez 10, Carbopol® 934, Carbopol® 940, Carbopol® 941, Carbopol® 1342, or any combination thereof.

According to certain embodiments, the crosslinked acrylic acid polymer is an acrylic acid homopolymer cross-linked with allyl ethers of sucrose. In certain aspects, an acrylic acid homopolymer cross-linked with allyl ethers of sucrose may have an average of from 4 to 6 allyl groups per sucrose molecule. For example, the crosslinked acrylic acid polymer may be Carbopol® 974P polymer.

In other aspects, the crosslinked acrylic acid polymer is an acrylic acid homopolymer cross-linked with allyl ethers of pentaerythritol. Such acrylic acid homopolymers cross-linked with allyl ethers of pentaerythritol that may be present in the active agent layer of the subject transdermal compositions include, but are not limited to, Carbopol® 974P polymer.

According to certain embodiments, the crosslinked acrylic acid polymer is an acrylic acid homopolymer cross-linked with divinyl glycol. For example, acrylic acid polymers crosslinked with divinyl glycol that may be present in the first active agent layer include, but are not limited to, Noveon® AA-1 Polycarbophil polymer (Lubrizol Corp., Wickliffe, Ohio).

While the molecular weight of the crosslinked acrylic acid polymers may vary, in some instances the molecular weight ranges from 1,000 to 100,000,000, such as 3,000 to 10,000,000, and including 10,000 to 5,000,000.

In certain aspects, the crosslinked acrylic acid polymer is present in the first active agent layer in an amount of from 1% to 30% w/w, such as from 1% to 20% w/w, such as from 1% to 10% w/w, such as from 2% to 8% w/w, including from 3% to 7% w/w, e.g., from 4% to 6% w/w. According to certain embodiments, the crosslinked acrylic acid polymer is present in the active agent layer in an amount of from 2% w/w or more, 3% w/w or more, 4% w/w or more, 5% w/w or more, 6% w/w or more, 7% w/w or more, 8% w/w or more, 9% w/w or more, 10% w/w or more, 11% w/w or more, 12% w/w or more, 13% w/w or more, 14% w/w or more, or 15% w/w or more. In certain aspects, the crosslinked acrylic acid polymer is present in the active agent layer in an amount of from 10% w/w or less, 9% w/w or less, 8% w/w or less, 7% w/w or less, 6% w/w or less, 5% w/w or less, 4% w/w or less, 3% w/w or less, or 2% w/w or less.

The active agent layer may include additional components. For example, the active agent layer may include one or more polymeric components in addition to the crosslinked acrylic acid polymer. Non-crosslinked acrylic acid polymers of interest include, but are not limited to, copolymers of butyl methacrylate and methyl methacrylate. According to certain embodiments, the active agent layer includes a copolymer of butyl methacrylate and methyl methacrylate present in an amount of from 2% to 30% w/w, from 5% to 25% w/w, from 10% to 20% w/w, including 15% w/w. In certain aspects, the copolymer of butyl methacrylate and methyl methacrylate is Plastoid® B copolymer having the formula:

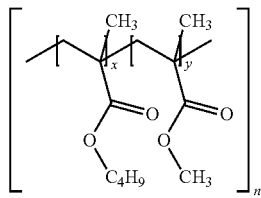

The active agent layer may further include a pressure-sensitive adhesive. The term "pressure sensitive adhesive" means an adhesive that forms a bond when pressure is applied to adhere the adhesive with a surface. In some instances, the adhesive is one in which no solvent, water, or heat is needed to activate the adhesive. For pressure sensitive adhesives, the degree of bond strength is proportional to the amount of pressure that is used to apply the adhesive to the surface.

Pressure sensitive adhesives of interest include acrylate copolymers present in an organic solvent. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include crosslinked and non-cross-linked polymers. The polymers can be cross-linked by known methods to provide the desired polymers.

Monomers from which the acrylate copolymers are produced include at least two or more exemplary components selected from the group including acrylic acids, alkyl acrylates, methacrylates, copolymerizable secondary monomers. Monomers ("soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989).

In certain aspects, the pressure-sensitive adhesive is a copolymer, such as an acrylate copolymer. Acrylate copolymer-based pressure-sensitive adhesives of interest include, but are not limited to, Duro-Tak® and Gelva® pressure-sensitive adhesives. According to certain embodiments, the active agent layer includes an acrylate copolymer-based pressure sensitive adhesive selected from Duro-Tak® 87-2353, Duro-Tak® 387-2353, Duro-Tak® 87-900A, Duro-Tak® 87-9301, Duro-Tak® 87-4098, Duro-Tak® 87-2510, Duro-Tak® 387-2510, Duro-Tak® 87-2287, Duro-Tak® 387-2287, Duro-Tak® 87-4287, Duro-Tak® 87-2516, Duro-Tak® 387-2516, Duro-Tak® 87-2074, Duro-Tak® 87-235A, Duro-Tak® 87-2852, Duro-Tak® 87-2051, Duro-Tak® 387-2051, Duro-Tak® 87-2052, Duro-Tak® 387-2052, Duro-Tak® 87-2054, Duro-Tak® 387-2054, Duro-Tak® 87-2194, Duro-Tak® 87-2196, Gelva® GMS 3083, Gelva® GMS 3253, Gelva® GMS 788, Gelva® GMS 9073, or any combination thereof. Polyisobutylenes (PIB), silicones, and styrene-isoprene-styrenes (SIS) (e.g., Kraton® SIS polymers) may also be included, e.g., as desired.

According to certain embodiments, when the active agent layer includes a pressure-sensitive adhesive, the pressure-sensitive adhesive is present in an amount of from 5% to 80% w/w (e.g., from 5 to 75% w/w), such as from 20% to 80% w/w, such as from 25% to 75% w/w, such as from 40% to 60%, including from 45% to 55%, e.g., from 49% to 51% w/w.

In certain aspects, the active agent layer includes an antioxidant. Any suitable antioxidant may be employed in the active agent layer. According to certain embodiments, the active agent layer includes an antioxidant selected from vitamin E, or other tocopherol analogs, including tocopherol acetate or TPGS, citric acid, ascorbic acid, sodium sulfite, ascorbyl palmitate, sodium metasulfite, alkyl gallate, or any combination thereof. The antioxidant may be present in any desired amount, including from 0.01% to 5.0%, such as from 0.05% to 3%, including from 0.075% to 1%, e.g., 0.1%.

In certain aspects, the first active agent layer that includes a crosslinked acrylic acid, e.g., as described above, includes substantially little, if any, water. By "substantially little" is meant 2.5% (w/w) or less, such as 1.5% (w/w) or less, 1.0% (w/w) or less, 0.5% (w/w) or less, 0.25% (w/w) or less, including no solvents, e.g., water. According to certain embodiments, the active agent layer does not include any water, i.e., the adhesive layer includes 0% water.

Adhesive Layer

As summarized above, the transdermal compositions of the present disclosure may include one or more layers in addition to the active agent layer. For example, the compositions may include an adhesive layer, e.g., disposed on a side of the active agent layer opposite the backing. According to certain embodiments, when a transdermal composition of the present disclosure includes an adhesive layer, the adhesive layer may have a coat weight of from 0.5 mg/cm$^2$ to 8 mg/cm$^2$, such as from 1 mg/cm$^2$ to 7 mg/cm$^2$, such as from 1.5 mg/cm$^2$ to 6 mg/cm$^2$, including from 2 mg/cm$^2$ to 5 mg/cm$^2$, such as from 2.5 mg/cm$^2$ to 4 mg/cm$^2$, e.g., 3 mg/cm². The dimensions of the adhesive layer may be the same or different as compared to the dimensions of the active agent layer. For example, the dimensions (cm²) of the adhesive layer may be the same, larger, or smaller than the active agent layer. According to certain embodiments, the dimensions of the adhesive layer range from 5 to 75 cm², such as from 10 to 50 cm², e.g., 20 to 40 cm².

The adhesive layer may be made of any suitable components. In certain aspects the adhesive layer includes a pressure-sensitive adhesive. The pressure sensitive adhesive may be present in an amount of from 50% to 100%, such as from 75% to 100%, such as from 85% to 100%, such as from 90% to 100%, including 95% to 100%, e.g., 99% to 100% (e.g., 98.9% or 99.9%) (It is noted that these percentages are percentages after removal of solvents, e.g., via evaporation).

In certain aspects, the pressure-sensitive adhesive is a polymeric adhesive, such as an acrylate copolymer adhesive. Acrylate copolymer adhesives that find use in the compositions of the present disclosure include, but are not limited to, Duro-Tak® and Gelva® pressure-sensitive adhesives. When the adhesive layer includes an acrylate copolymer-based pressure-sensitive adhesive, the acrylate copolymer may lack pendant functional groups (e.g., the copolymer does not include —COOH and/or —OH functional groups). Non-limiting examples of pressure-sensitive adhesives that lack pendant functional groups include Duro-Tak® 87-900A, Duro-Tak® 87-9301, Duro-Tak® 87-4098, Gelva® GMS 3083, Gelva® GMS 3253, and combinations thereof.

When the adhesive layer includes an acrylate copolymer-based pressure-sensitive adhesive, the acrylate copolymer may include pendant functional groups (e.g., the copolymer includes —COOH and/or —OH functional groups). Non-limiting examples of pressure sensitive adhesives that include pendant functional groups include Duro-Tak® 87-2510, Duro-Tak® 387-2510, Duro-Tak® 87-2287, Duro-Tak® 387-2287, Duro-Tak® 87-4287, Duro-Tak® 87-2516, Duro-Tak® 387-2516, Duro-Tak® 87-2074, Duro-Tak® 87-235A, Duro-Tak® 87-2353, Duro-Tak® 387-2353, Duro-Tak® 87-2852, Duro-Tak® 87-2051, Duro-Tak® 387-2051, Duro-Tak® 87-2052, Duro-Tak® 387-2052, Duro-Tak® 87-2054, Duro-Tak® 387-2054, Duro-Tak® 87-2194, Duro-Tak® 87-2196, Gelva® GMS 788, and Gelva® GMS 9073.

In certain aspects, the adhesive layer includes a silicone-based pressure-sensitive adhesive (e.g., a pressure-sensitive adhesive that includes silicone). Silicone-based pressure-sensitive adhesives of interest include, but are not limited to, adhesives produced through a condensation reaction of a silanol end-blocked polydimethylsiloxanes (PDMS) with a silicate resin. The residual silanol functionality may then be capped with trimethylsiloxy groups to yield the chemically stable amine-compatible adhesive. Such adhesives may have the formula:

Non-limiting examples of such silicone-based pressure-sensitive adhesives include commercially available adhesives sold under the trade name BIO-PSA (Dow Corning®, Midland, Mich.) and include BIO-PSA 7-4301, BIO-PSA 7-4302, BIO-PSA 7-4101, BIO-PSA 7-4201, BIO-PSA 7-4102, and BIO-PSA 7-4202. In certain aspects, the pressure-sensitive adhesive of the adhesive layer is an adhesive that includes polybutene (e.g., polyisobutylene (PIB)). Such adhesives may further include a tackifier. For example, an adhesive that may be included in the adhesive layer of the transdermal compositions of the present disclosure is an adhesive that includes Panalane® polyisobutene.

The adhesive layer may include any suitable pressure sensitive adhesive, either alone or in combination with any other pressure-sensitive adhesive. For example, the adhesive layer may include a single species of pressure-sensitive adhesive selected from Duro-Tak® 9301 and BIO-PSA 7-4302. In other aspects, the adhesive layer may include a combination (e.g., a blend) of pressure-sensitive adhesives, including any combination of two or more of the acrylate copolymer-based and/or silicon-based pressure-sensitive adhesives described above.

According to certain embodiments, the adhesive layer includes an antioxidant. Any suitable antioxidant may be employed in the adhesive layer. In certain aspects, the active agent layer includes an antioxidant selected from vitamin E analogs, including tocopherol acetate of TPGS, citric acid, ascorbic acid, sodium sulfite, ascorbyl palmitate, sodium metabisulfite, alkyl gallate, or any combination thereof. The antioxidant may be present in any desired amount, including from 0.01% to 0.5%, such as from 0.05% to 0.25%, including from 0.075% to 0.2%, e.g., 0.1%.

Additional components that may be included in the adhesive layer include, e.g., an oil. The amount of oil in the adhesive layer may vary, and in certain aspects, is selected to achieve an adhesive layer having a desired tack. According to certain embodiments, the oil is present in an amount of from 0.1% to 5% w/w, such as from 0.5% to 2.5% w/w, including from 0.75% to 1.5% w/w, e.g., 1% w/w. Oils of interest include, but are not limited to, silicone oil (e.g., Q7-9120 silicone fluid (Dow Corning®, Midland, Mich.)).

Any layer in the transdermal compositions of the present disclosure may contain a percutaneous absorption enhancer. The percutaneous absorption enhancer may facilitate the absorption of rivastigmine by the skin of the subject. The percutaneous absorption enhancer may also be referred to as a percutaneous permeation enhancer because it may facilitate not only the percutaneous absorption of the rivastigmine, but also the percutaneous permeation of the rivastigmine through the skin of the subject.

The percutaneous absorption enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropa-

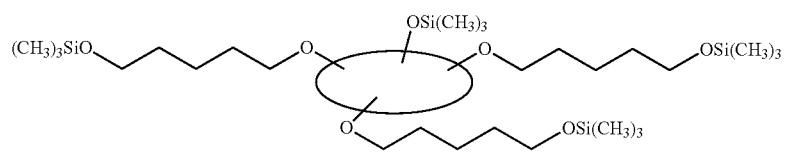

nolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —O—$CH_2CH_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of percutaneous absorption enhancers include, but are not limited to lactic acid, tartaric acid, 1,2,6-hexanetriol, benzyl alcohol, lanoline, potassium hydroxide (KOH), and tris(hydroxymethyl)aminomethane.

Specific examples of percutaneous absorption enhancers include, but are not limited to glycerol monooleate (GMO), sorbitan monolaurate (SML), sorbitan monooleate (SMO), laureth-4 (LTH), and combinations thereof.

In some cases, the layer (e.g., the active agent layer and/or the adhesive layer) contains the percutaneous absorption enhancer in an amount ranging from 2% to 25% (w/w), such as from 5% to 20% (w/w), and including from 5% to 15% (w/w). In certain cases, a layer contains the percutaneous absorption enhancer in an amount of about 5% (w/w), about 10% (w/w), about 15% (w/w), or about 20% (w/w).

In certain aspects, the transdermal compositions of the present disclosure do not include a percutaneous absorption or permeation enhancer.

Second Active Agent Layer

In certain aspects, the transdermal compositions of present disclosure include a second rivastigmine-containing active agent layer, e.g., present between the first active agent layer and the backing. The second active agent layer may include any of the features described above with respect to the first active agent layer. For example, the second active agent layer may include any of the polymeric components (e.g., one of more crosslinked acrylic acid polymers, one or more copolymers (e.g., copolymers of butyl methacrylate and methyl methacrylate), pressure-sensitive adhesive polymers), anti-oxidants, and the like as described above.

In certain aspects, a rivastigmine transdermal composition of the present invention is a three-layer composition that includes a first active agent layer that includes a crosslinked acrylic acid polymer, an adhesive layer, and a second active agent layer which may or may not include a crosslinked acrylic acid polymer, where the second active agent layer is disposed on a side of the first active agent layer opposite the adhesive layer, e.g., between a backing and the first active agent layer. The coat weight of the second active agent layer may vary. In certain aspects, the coat weight of the second active agent layer is from 2.5 mg/$cm^2$ to 25 mg/$cm^2$. According to certain embodiments, the second active agent layer does not include a crosslinked acrylic acid polymer.

According to certain embodiments, the second active agent layer does not include water, i.e., the second active agent layer includes 0% water.

Membrane or Support Layer

According to certain embodiments, a transdermal composition of the present disclosure includes one or more membranes. When the composition includes a membrane, the membrane may be disposed between two layers of the composition, within a layer of the composition (e.g., within an active agent layer or within an adhesive layer), or in any other desirable configuration. For example, when the transdermal composition is a two-layer composition that includes a first active agent layer and an adhesive layer, a membrane may be disposed between the first active agent layer and the adhesive layer. Also by way of example, when the transdermal composition is a three-layer composition that includes a first active agent layer, a second active agent layer, and an adhesive layer, a membrane may be disposed between the first active agent layer and the second active agent layer, between the first active agent layer and the adhesive layer, or both.

In certain aspects, including a membrane in a transdermal composition of the present invention results in higher controlled release of the active agent and/or reduces or eliminates any "cold flow" exhibited by the composition in the absence of the membrane. Cold flow is an aspect of certain pressure-sensitive adhesives in which the adhesive migrates out of the edge of a transdermal composition (e.g., a patch) during storage or when the composition is applied to a patient. Excessive cold flow may result in excessive sticking to the inside surfaces of any packaging in which the composition is stored, separation of the release liner during removal of the composition from the packaging, deposition of the adhesive around the periphery of the composition on the skin of a patient to which the composition is applied, and/or the like.

When one or more membranes are employed in the transdermal compositions of the present disclosure, the membrane may be made from any suitable material. In certain aspects, the membrane is made of a material selected from monolayer polypropylene (e.g., Celgard® PP monolayer polypropylene membrane), polyethylene (e.g., Celgard® PE polyethylene membrane), a vinyl acetate-containing material (e.g., 3M™ Colran™ vinyl acetate film, such as 3M™ Colran™ 9707 film, 3M™ Colran™ 9726 film, and/or the like), a non-woven or woven sheet, or any combination thereof.

Backing

As summarized above, transdermal compositions of interest may include a backing (i.e., support layer). The backing may be flexible to an extent that it can be brought into close contact with a desired topical location of a subject. The backing may be fabricated from a material that it does not absorb the active agent, and does not allow the active agent to be released from the side of the support. The backing may include, but is not limited to, non-woven fabrics, woven fabrics, films (including sheets), porous bodies, foamed bodies, paper, composite materials obtained by laminating a film on a non-woven fabric or fabric, and combinations thereof. The backing layer may also be layered to another adhesive layer, for example a PIB adhesive layer may be used as an occlusive layer.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric.

The size of the backing may vary, and in some instances the backing is sized to cover the desired topical target site. In some embodiments, the backing has a length ranging from 2 to 100 cm, such as 4 to 60 cm and a width ranging from 2 to 100 cm, such as 4 to 60 cm.

In some embodiments, the backing layer is insoluble in water. By insoluble in water is meant that that the backing layer may be immersed in water for a period of 1 day or longer, such as 1 week or longer, including 1 month or longer, and exhibit little if any dissolution, e.g., no observable dissolution.

Release Liner

As summarized above, in some embodiments, the transdermal compositions of the present disclosure include a release liner. In certain aspects, when it is desirable for the active agent layer to make direct contact with a skin surface of a subject, the release liner may be disposed directly on the active agent layer and removed prior to use (see, e.g., FIG. 1). In other aspects, when one or more additional layers are present in the composition (e.g., an adhesive layer), the release liner may be disposed directly on the adhesive layer and removed prior to use (see, e.g., FIG. 2).

The release liner facilitates the protection of the active agent layer and/or any additional layers (e.g., an adhesive layer, if present) of the transdermal compositions. In certain aspects, a release liner may be prepared by treating one side of polyethylene-coated wood free paper, polyolefin-coated glassine paper, a polyethylene terephthalate (polyester) film, a polypropylene film, or the like with a silicone treatment.

Adhesive Overlay

Optionally, one or more adhesive overlays can be used to increase the adhesion of the composition when applied to the skin. Adhesive overlays can include a layer of adhesive present on a backing material, such as a porous, non-porous, occlusive, or breathable backing material. The dimensions of the adhesive overlay are chosen to provide the desired functionality, where in some instances the dimensions are chose such that the adhesive overlay, when applied over the active agent formulation, extends some distance beyond one or more of the sides of the active agent formulation. In some instances, the area of the adhesive overlay exceeds the area of the active agent layer by 5% or more, such as by 10% or more, including by 20% or more. During use, the adhesive overlay can be applied by the patients, by the care givers, or can be integrated in the kits.

Methods of Use

As summarized above, methods that employ the transdermal compositions of the present disclosure are provided. According to certain embodiments, the methods include applying to a skin site of a subject any of the transdermal compositions described herein, in a manner sufficient to achieve a therapeutic flux of the rivastigmine for an extended period of time. In certain aspects, the therapeutic flux ranges from 1 to 40 μg/cm$^2$/hr, such as from 1 to 20 μg/cm$^2$/hr, such as from 2 to 20 μg/cm$^2$/hr, such as from 2 to 15 μg/cm$^2$/hr, including from 5 to 15 μg/cm$^2$/hr, e.g., for an extended period of time (e.g., from 2 to 10 days, including 5 or more days, e.g., 7 or more days).

Methods of using the transdermal compositions include administering an effective amount of rivastigmine to a subject in order to treat the subject for a target condition of interest, e.g., as described in the Utility section below. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the transdermal compositions disclosed herein can be topically administered to a subject, i.e., the transdermal compositions may be administered to any convenient topical site (e.g., skin site). Topical sites of interest include both mucosal sites and keratinized skin sites, and therefore include, but are not limited to: arms, torso (e.g., chest or back), legs, head, mouth, nose, eyes, rectum, vagina, etc. The surface area that is covered by the topical composition following application is sufficient to provide for the desired amount of agent administration, and in some embodiments ranges from 1 to 400 cm$^2$, such as from 1 to 300 cm$^2$, such as from 1 to 200 cm$^2$, such as from 10 to 180 cm$^2$ (e.g., from 20 to 50 cm$^2$) and including from 100 to 150 cm$^2$, e.g., 140 cm$^2$.

The transdermal composition may be maintained at the topical site to which it has been applied for a desired amount of time, e.g., to deliver a desired amount of active agent delivery. In some instances, the period of time that the composition is maintained at the site of application is 24 hours or longer, such as 48 hours or longer, including 72 hours or longer, e.g., 96 hours or longer, including 120 hours or longer, such as 144 hours or longer, e.g., 168 hours or longer, including 240 hours or longer. In certain aspects, a transdermal composition of the present disclosure is maintained at the topical site to which it has been applied for an extended period of time that is from 2 to 10 days (e.g., 7 days).

In practicing the subject methods, a given dosage of the transdermal composition may be applied a single time or a plurality of times over a given time period, e.g., the course of the disease condition being treated, where the dosing schedule when a plurality of compositions are administered over a given time period may be daily, weekly, biweekly, monthly, etc.

After the transdermal active agent composition has been applied to the skin site for the desired amount of time (i.e., an amount of time sufficient to deliver a target dose of the rivastigmine to the subject over a period of time), the composition may be removed from the skin site. A new transdermal composition may be applied at the same or at a different skin site. The new transdermal composition may be applied to a different skin site to reduce the possible occurrence of skin irritation and/or skin sensitization at the prior site of application.

In certain embodiments, the subject methods include a diagnostic step. Individuals may be diagnosed as being in need of the subject methods using any convenient protocol. In addition, individuals may be known to be in need of the subject methods, e.g., they are suffering from memory problems, such as dementia, including dementia associated with Alzheimer's disease or Parkinson's disease. Diagnosis or assessment of target condition can be performed using any convenient diagnostic protocol.

Methods of the present disclosure may further include assessing the efficacy of the treatment protocol that includes transdermal administration of rivastigmine. Assessing the efficacy of treatment may be performed using any convenient protocol, and in certain embodiments, includes a protocol to assess the memory of the subject or other symptoms associated with, e.g., Alzheimer's disease or Parkinson's disease.

In some instances, transdermal compositions may be administered in conjunction with one or more additional therapies specific for the target condition of interest. As such, the transdermal compositions may be used alone to treat the target disorder, or alternatively, as in the case of Alzheimer's disease, for example, they may be used as an adjunct to the conventional cholinesterase inhibitor and/or memantine therapies. As in the case of Parkinson's disease, for example, they may be used as an adjunct to the conventional L-DOPA treatments.

Transdermal compositions of the present disclosure may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The transdermal compositions of the present disclosure find use in any application where a subject would benefit from transdermal administration of rivastigmine. Rivastigmine finds use in the treatment of a variety of different disease conditions, such as but not limited to: diseases associated with memory loss, such as dementia, including dementia associate with Alzheimer's disease, dementia associated with Parkinson's disease, and the like. By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Kits

Kits for use in practicing certain methods described herein are also provided. In certain aspects, the kits include one or more of any of the transdermal compositions described elsewhere herein. According to certain aspects, the kits include two or more of the subject transdermal compositions. In a given kit that includes two or more compositions, the compositions may be individually packaged or present within a common container, where the packaging and/or container may be sterile, e.g., a sterile pouch.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out aspects of the present disclosure. The examples are for illustrative purposes only, and are not intended to limit the scope of the present disclosure in any way.

EXAMPLES

I. Materials and Methods

A. Preparation of Transdermal Compositions that Include a Rivastigmine-Containing Active Agent Layer and an Adhesive Layer To prepare the active agent layer, rivastigmine, excipients, and organic solvents to adjust the coat mix were weighed in a container and mixed to obtain a homogenous active agent layer solution. (e.g., Vitamin E, a Carbomer (e.g., Carbopol 974P), Rivastigmine, Ethyl-acetate are added to a suitable container, and then mixed well. When the resultant mix is consistent, Plastoid B pre-dissolved in Ethyl Acetate, and adhesive, are added to the mixture to produce a solution). The solution was poured on to the release coated side of a release liner, and casted using a drawdown coating machine (GARDCO® Automatic Drawdown Machine 2). The gauge of the coating bar was set to obtain the target coat thickness. The release liner with casted adhesive mix was dried in an oven (BINDER, FEP 115-VL) at 75° Celsius for 12 minutes to obtain a sheet of active agent layer, and laminated with a backing. The release liner is then removed to laminate the adhesive side with the adhesive layer prepared as described below.

For the preparation of the skin adhesive layer, Vitamin E and pressure-sensitive adhesive (e.g., Duro-tak 9301, Bio-PSA 4302) were added to a container, followed by addition of ethyl acetate to reach the desired solid content weight % (for example 20%-50%, such as 30%-40%). After mixing, the mixture was poured on to the release coated side of the release liner, casted using a drawdown coating machine at the desired coat weight and thickness, and dried in an oven at 75° Celsius (where a suitable range is 70±5° Celsius) for 12 minutes to obtain a sheet of skin adhesive layer.

Upon preparation of the sheets of active agent layer and skin adhesive layer, the adhesive side of active agent layer and skin adhesive layer were laminated together, and transdermal compositions were punched out at the desired sizes ($cm^2$).

The composition presented in specific example was prepared on weight basis ($mg/cm^2$). The formulation may be presented in thickness basis (μm) for convenience assuming a density of 1.0 $g/cm^3$ B. Transdermal Flux Tests For transdermal flux tests, the epidermis of human cadaver skin was isolated and punched out at the desired size. The prepared epidermis was placed onto a 10 mL vertical-type Frantz cell, and the transdermal patch punched out at the desired size was applied and checked carefully for pinholes or air bubbles. Phosphate Buffer (TAKARA BIO, PBS tablet, pH 7.5) with 0.01% Gentamicine as antibiotic was filled into the Frantz cell as a receptor solution. At each sampling time, the full 10 mL of receptor solution was removed from the vertical type Frantz cell, and replaced with new 10 mL receptor solution. A portion of the collected samples were analyzed by HPLC using an XDB-C18 column (column size 4.6 mm×50 mm, particle size: 5 μm) on an AGILENT 1200 LC System. 20 μL of sample was injected and interrogated at 215 nm wavelength. The mobile phase included 75 mM $(NH_4)_2HPO_4$ (pH=7.00), acetonitrile, and MeOH in a 2:1:1 ratio, respectively.

II. Specific Examples

A. Flux of Various Transdermal Compositions

1. The Effect of Active Agent Layer Coat Weight on the Flux of Rivastigmine

The effect of active agent layer coat weight on the flux of rivastigmine was assessed using formulations having an active agent layer coat weight of 12 $mg/cm^{2,}$ 18 $mg/cm^2$, and 24 $mg/cm^2$. The specific make-up of these compositions is shown in Table 1 below.

Figure 4:
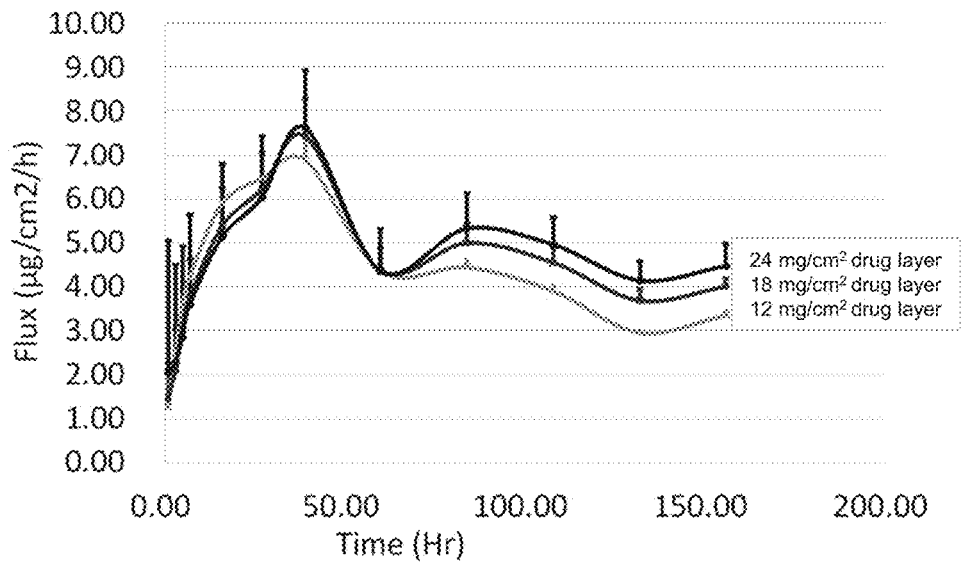
FIG. 4 shows a graph of the rivastigmine flux characteristics of example two-layer transdermal compositions differing with respect to the coat weight of the active agent layer.

The results, shown in FIG. 4, indicate a positive correlation between active agent layer thickness and sustained release of rivastigmine at day 7.

2. The Effect of Crosslinked Acrylic Acid Polymer on the Flux of Rivastigmine

The effect of the presence and amount of crosslinked acrylic acid polymer on the flux of rivastigmine was assessed using formulations having an active agent layer coat weight of 12 $mg/cm^2$). Specifically, the flux of transdermal compositions including 3% w/w Carbopol, 5% Carbopol, and 7% Carbopol were compared to a composition that does not include a crosslinked acrylic acid polymer in the active agent layer or the adhesive layer (the 1-day Exelon® patch marketed by Novartis (Basel, CH)). The specific make-up of these compositions is shown in Table 2 below. (When the drug loading XX $mg/cm^2$ is fixed, the dry thickness of the adhesive becomes thinner (lower $mg/cm^2$) as the drug loading wt % is higher. Drug loading mg/cm2 is dry adhesive thickness ($mg/cm^2$)*drug loading wt %)

TABLE 2

Figure 5:
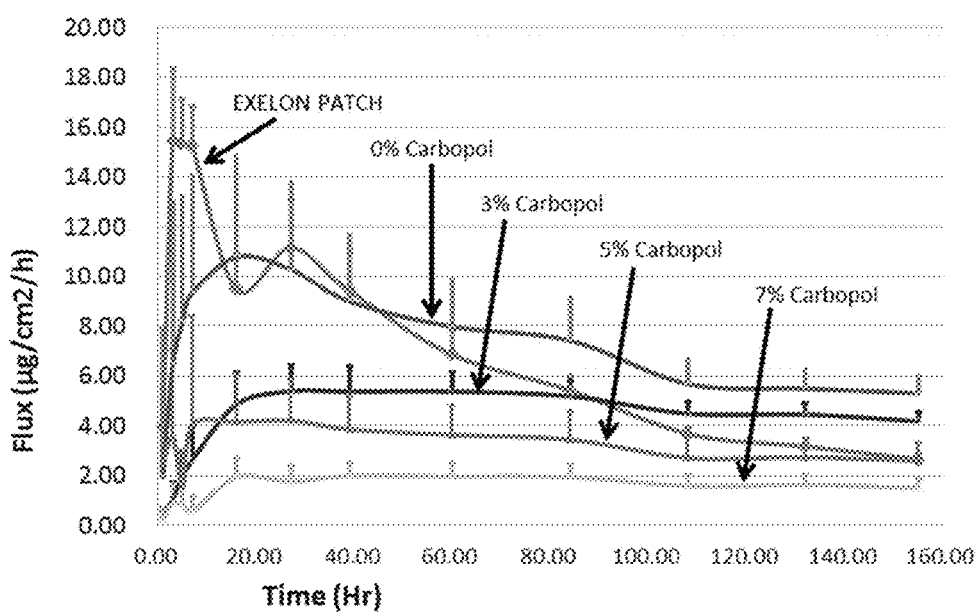
FIG. 5 shows a graph of the rivastigmine flux characteristics of example two-layer transdermal compositions having differing amounts of crosslinked acrylic acid polymer in the active agent layer, as well as a patch having no crosslinked acrylic acid polymer in the active agent layer.

| | Transdermal compositions shown in FIG. 5 | | | |
|---|---|---|---|---|
| | Composition 4 | Composition 5 | Composition 6 | Composition 7 |
| Active Agent Layer | 30% Rivastigmine<br>20% Plastoid<br>0% Carbopol 974P<br>0.1% Vitamin E<br>49.9% Duro-Tak 2353<br>24 $mg/cm^2$ coat weight | 30% Rivastigmine<br>17% Plastoid<br>3% Carbopol 974P<br>0.1% Vitamin E<br>49.9% Duro-Tak 2353<br>24 $mg/cm^2$ coat weight | 30% Rivastigmine<br>15% Plastoid<br>5% Carbopol 974P<br>0.1% Vitamin E<br>49.9% Duro-Tak 2353<br>24 $mg/cm^2$ coat weight | 30% Rivastigmine<br>13% Plastoid<br>7% Carbopol 974P<br>0.1% Vitamin E<br>49.9% Duro-Tak 2353<br>24 $mg/cm^2$ coat weight |
| Adhesive Layer | 99.9% Duro-Tak 9301<br>0.1% Vitamin E<br>3 $mg/cm^2$ coat weight | 99.9% Duro-Tak 9301<br>0.1% Vitamin E<br>3 $mg/cm^2$ coat weight | 99.9% Duro-Tak 9301<br>0.1% Vitamin E<br>3 $mg/cm^2$ coat weight | 99.9% Duro-Tak 9301<br>0.1% Vitamin E<br>3 $mg/cm^2$ coat weight |

As shown in FIG. 5, the presence of crosslinked acrylic acid polymer in the active agent layer unexpectedly results in the compositions having a significantly altered flux profile as compared to the 1-day Exelon® patch, which does not include a crosslinked acrylic acid polymer in the active agent layer (or adhesive layer). The graph shown in FIG. 5 indicates that the flux characteristics are affected by the amount of crosslinked acrylic acid polymer in the active agent layer, and that the crosslinked acrylic acid polymer results in more sustained release of the rivastigmine on day 7 as compared to day 1. The composition that does not include crosslinked acrylic acid polymer shows a prominent decrease in flux over the course of the 7-day study.

3. Rivastigmine Flux of Compositions Having Different Crosslinked Acrylic Acid Polymers The flux characteristics of three example compositions in accordance with the present disclosure were evaluated. In

TABLE 1

| | Transdermal compositions shown in FIG. 4 | | |
|---|---|---|---|
| | Composition 1 | Composition 2 | Composition 3 |
| Active Agent Layer | 30% Rivastigmine<br>15% Plastoid<br>5% Carbopol 934P<br>0.1% Vitamin E<br>49.9% Duro-Tak 2353<br>12 $mg/cm^2$ coat weight | 30% Rivastigmine<br>15% Plastoid<br>5% Carbopol 934P<br>0.1% Vitamin E<br>49.9% Duro-Tak 2353<br>18 mg/cm2 coat weight | 30% Rivastigmine<br>15% Plastoid<br>5% Carbopol 934P<br>0.1% Vitamin E<br>49.9% Duro-Tak 2353<br>24 $mg/cm^2$ coat weight |
| Adhesive Layer | 98.9% BIO-PSA 4302<br>1.0% 9120 Silicon Oil<br>0.1% Vitamin E<br>3 $mg/cm^2$ coat weight | 98.9% BIO-PSA 4302<br>1.0% 9120 Silicon Oil<br>0.1% Vitamin E<br>3 $mg/cm^2$ coat weight | 98.9% BIO-PSA 4302<br>1.0% 9120 Silicon Oil<br>0.1% Vitamin E<br>3 $mg/cm^2$ coat weight | this example, the compositions included differing cross-linked acrylic acid polymers present in an amount of 5% w/w. The specific make-up of these compositions is shown in Table 3 below.

Figure 7:
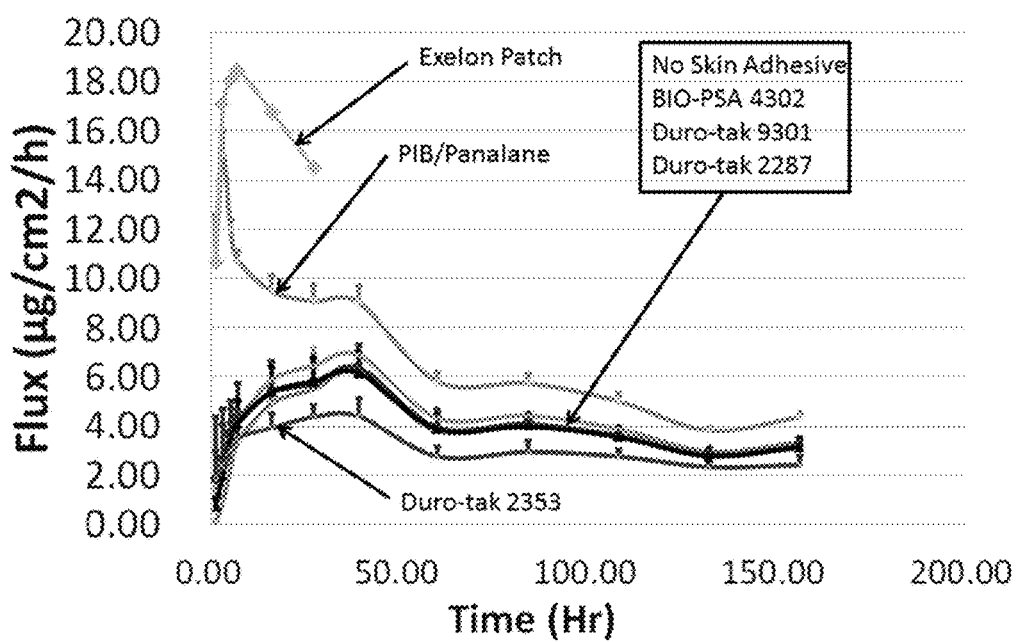
FIG. 7 shows a graph of the rivastigmine flux characteristics of example two-layer transdermal compositions according to the present disclosure having 5% crosslinked acrylic acid polymer in the active agent layer, and different pressure sensitive adhesives in a skin adhesive layer.

As shown in FIG. 7, the composition having PIB-Panalane as the skin adhesive showed a greater initial flux, while the composition having Duro-Tak 2353 exhibited the lowest flux for the 7-day period. The fluxes were equivalent for compositions having Duro-tak 2287, Duro-tak 9301, and BIO-PSA 4302 as skin adhesive.

TABLE 3

Figure 6:
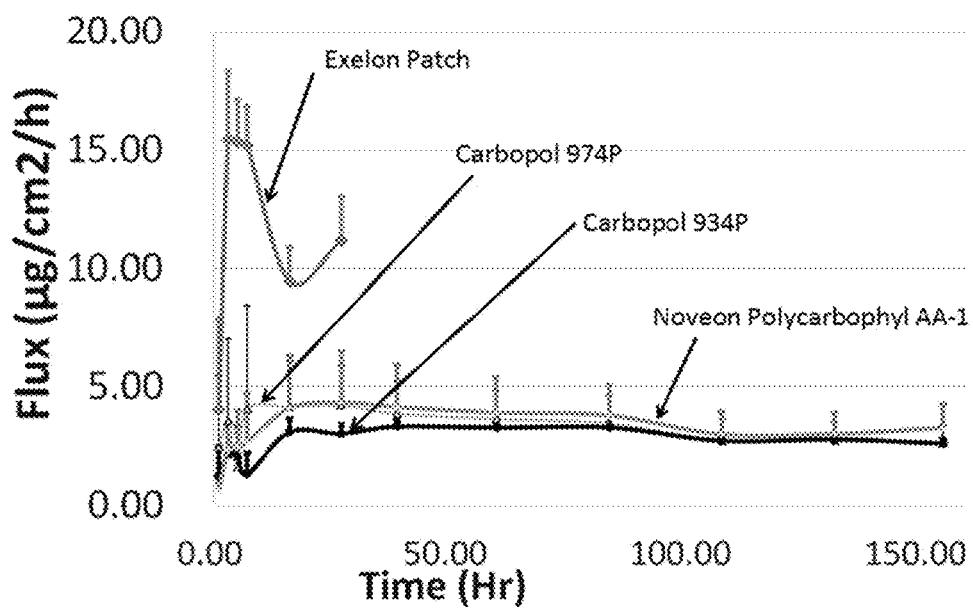
FIG. 6 shows a graph of the rivastigmine flux characteristics of example two-layer transdermal compositions in accordance with the present disclosure.

Transdermal compositions shown in FIG. 6

|  | Composition 8 | Composition 9 | Composition 10 |
|---|---|---|---|
| Active Agent Layer | 30% Rivastigmine<br>15% Plastoid<br>5% Carbopol 974P<br>0.1% Vitamin E<br>49.9% Duro-Tak 2353<br>24 mg/cm² coat weight | 30% Rivastigmine<br>15% Plastoid<br>5% Carbopol 934P<br>0.1% Vitamin E<br>49.9% Duro-Tak 2353<br>24 mg/cm² coat weight | 30% Rivastigmine<br>15% Plastoid<br>5% AA-1 Polycarbophil<br>0.1% Vitamin E<br>49.9% Duro-Tak 2353<br>24 mg/cm² coat weight |
| Adhesive Layer | 99.9% Duro-Tak 9301<br>0.1% Vitamin E<br>3 mg/cm² coat weight | 99.9% Duro-Tak 9301<br>0.1% Vitamin E<br>3 mg/cm² coat weight | 99.9% Duro-Tak 9301<br>0.1% Vitamin E<br>3 mg/cm² coat weight |

As shown in FIG. 6, each of the formulations exhibited a sustained flux for 7 days, while the Exelon® patch exhibited a marked decrease in flux after day 1.

4. Rivastigmine Flux of Compositions Having Different Skin Adhesive Layers

The flux characteristics of six example compositions in accordance with the present disclosure were evaluated. In this example, the compositions included an active agent layer having a crosslinked acrylic acid polymer present in an amount of 5% w/w, and differing skin adhesive layers. The specific make-up of these compositions is shown in Table 4 below.

5. Rivastigmine Flux of Compositions Having Three Layers

The flux characteristics of four example compositions having three layers—a first active agent layer that does include a crosslinked acrylic acid polymer, a second active agent layer that does not include a crosslinked acrylic acid polymer, and a skin adhesive layer—in accordance with the present disclosure were evaluated. The specific make-up of these compositions is shown in Table 5 below.

TABLE 4

Transdermal compositions shown in FIG. 7

|  | Composition 11 | Composition 12 | Composition 13 |
|---|---|---|---|
| Active Agent Layer | 30% Rivastigmine<br>15% Plastoid<br>5% Carbopol 934P<br>0.1% Vitamin E<br>49.9% Duro-Tak 2353<br>12 mg/cm² coat weight | 30% Rivastigmine<br>15% Plastoid<br>5% Carbopol 934P<br>0.1% Vitamin E<br>49.9% Duro-Tak 2353<br>12 mg/cm² coat weight | 30% Rivastigmine<br>15% Plastoid<br>5% Carbopol 934P<br>0.1% Vitamin E<br>49.9% Duro-Tak 2353<br>12 mg/cm² coat weight |
| Adhesive Layer | No adhesive layer | 98.9% BIO-PSA 4302<br>1.0% 9120 Silicon Oil<br>0.1% Vitamin E<br>3 mg/cm² coat weight | 99.9% PIB-Panalane<br>0.1% Vitamin E<br>3 mg/cm² coat weight |
|  | Composition 14 | Composition 15 | Composition 16 |
| Active Agent Layer | 30% Rivastigmine<br>15% Plastoid<br>5% Carbopol 934P<br>0.1% Vitamin E<br>49.9% Duro-Tak 2353<br>12 mg/cm² coat weight | 30% Rivastigmine<br>15% Plastoid<br>5% Carbopol 934P<br>0.1% Vitamin E<br>49.9% Duro-Tak 2353<br>12 mg/cm² coat weight | 30% Rivastigmine<br>15% Plastoid<br>5% Carbopol 934P<br>0.1% Vitamin E<br>49.9% Duro-Tak 2353<br>12 mg/cm² coat weight |
| Adhesive Layer | 99.9% Duro-Tak 9301<br>0.1% Vitamin E<br>3 mg/cm² coat weight | 99.9% Duro-Tak 2287<br>0.1% Vitamin E<br>3 mg/cm² coat weight | 99.9% Duro-Tak 2353<br>0.1% Vitamin E<br>3 mg/cm² coat weight |

TABLE 5

Figure 8:
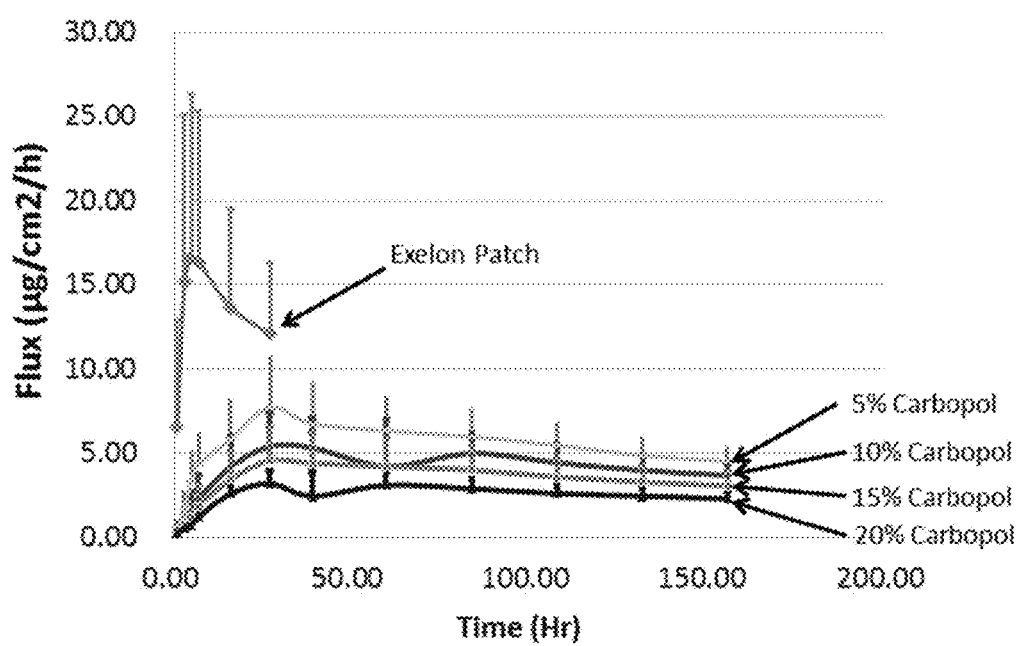
FIG. 8 shows a graph of the rivastigmine flux characteristics of example three-layer transdermal compositions in accordance with the present disclosure having a first active agent layer that does not include a crosslinked acrylic acid polymer, a second active agent layer that includes a crosslinked acrylic acid polymer, and a skin adhesive layer. The four examples shown have no crosslinked acrylic acid polymer in the first active agent layer and differing amounts of crosslinked acrylic acid polymer in the second active agent layer.

Three-layer transdermal compositions shown in FIG. 8

|  | Composition 17 | Composition 18 | Composition 19 | Composition 20 |
|---|---|---|---|---|
| 2nd Active Agent Layer | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight |
| 1st Active Agent Layer | 30% Rivastigmine<br>15% Plastoid<br>5% Carbopol 974P<br>49.9% Duro-Tak 2353<br>0.1% Vitamin E<br>3 mg/cm$^2$ coat weight | 30% Rivastigmine<br>10% Plastoid<br>10% Carbopol 974P<br>49.9% Duro-Tak 2353<br>0.1% Vitamin E<br>3 mg/cm$^2$ coat weight | 30% Rivastigmine<br>5% Plastoid<br>15% Carbopol 974P<br>49.9% Duro-Tak 2353<br>0.1% Vitamin E<br>3 mg/cm$^2$ coat weight | 30% Rivastigmine<br>0% Plastoid<br>20% Carbopol 974P<br>49.9% Duro-Tak 2353<br>0.1% Vitamin E<br>3 mg/cm$^2$ coat weight |
| Adhesive Layer | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight |

As shown in FIG. 8, the three-layer formulations exhibited a sustained flux for 7 days, while the Exelon® patch exhibited a marked decrease in flux after day 1.

6. Rivastigmine Flux of Three-Layer Compositions Having One or More Membranes

The flux characteristics of example compositions having three layers—a first active agent layer that does not include a crosslinked acrylic acid polymer, a second active agent layer that includes a crosslinked acrylic acid polymer, and a skin adhesive layer—and one or more membranes disposed between particular layers in accordance with the present disclosure were evaluated. The specific make-up of these compositions is shown in Table 6 below. As shown in Table 6, Composition 21 does not include a membrane between the first active agent layer and the second active agent layer, or between the second active agent layer and the skin adhesive layer. Composition 22 includes a membrane between the first active agent layer and the second active agent layer, and also between the second active agent layer and the skin adhesive layer. Composition 23 includes a membrane between the first active agent layer and the second active agent layer, but not between the second active agent layer and the skin adhesive layer. Composition 24 does not include a membrane between the first active agent layer and the second active agent layer, but includes a membrane between the second active agent layer and the skin adhesive layer.

TABLE 6

Figure 9:
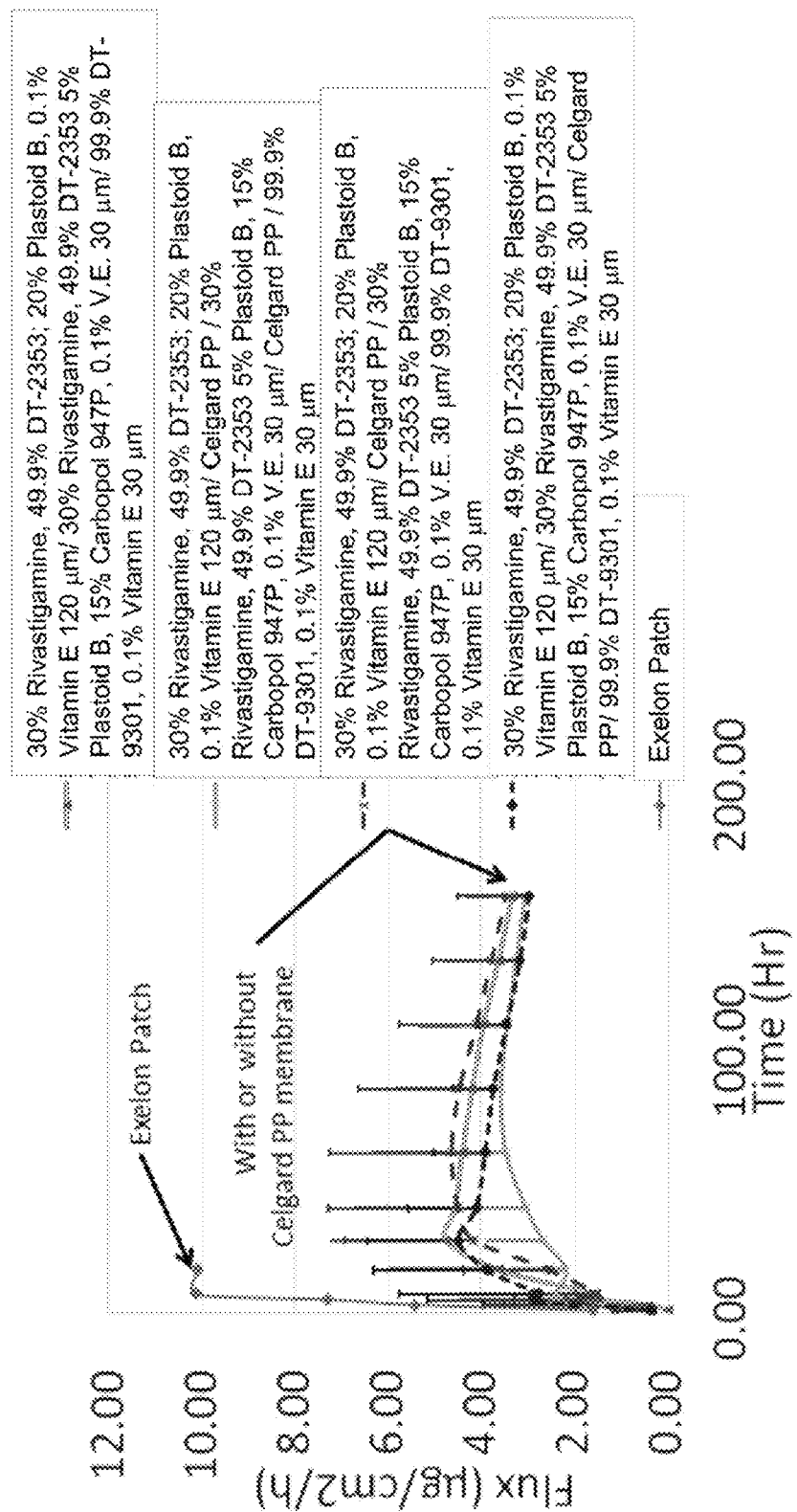
FIG. 9 shows a graph comparing the rivastigmine flux characteristics of membrane-containing and non-membrane-containing example transdermal compositions according to the present disclosure.

Three-layer transdermal compositions shown in FIG. 9

|  | Composition 21 | Composition 22 | Composition 23 | Composition 24 |
|---|---|---|---|---|
| 2nd Active Agent Layer | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight | 30% Rivastigmine<br>20% Plastoid<br>49.9% Duro-Tak 2353<br>0.1% Vitamin E<br>12 mg/cm$^2$ coat weight |
| Membrane | None | Celgard PP | Celgard PP | None |
| 1st Active Agent Layer | 30% Rivastigmine<br>5% Plastoid<br>15% Carbopol 974P<br>49.9% Duro-Tak 2353<br>0.1% Vitamin E<br>3 mg/cm$^2$ coat weight | 30% Rivastigmine<br>5% Plastoid<br>15% Carbopol 974P<br>49.9% Duro-Tak 2353<br>0.1% Vitamin E<br>3 mg/cm$^2$ coat weight | 30% Rivastigmine<br>5% Plastoid<br>15% Carbopol 974P<br>49.9% Duro-Tak 2353<br>0.1% Vitamin E<br>3 mg/cm$^2$ coat weight | 30% Rivastigmine<br>5% Plastoid<br>15% Carbopol 974P<br>49.9% Duro-Tak 2353<br>0.1% Vitamin E<br>3 mg/cm$^2$ coat weight |
| Membrane | None | Celgard PP | None | Celgard PP |
| Adhesive Layer | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight |

As shown in FIG. 9, the three-layer formulations having one or more membranes disposed between particular layers exhibited a sustained flux for 7 days, while the Exelon® patch exhibited a marked decrease in flux after day 1.

7. Rivastigmine Flux of Formulation Comprising Ethylene Vinyl Acetate/Vinyl Acetate Membrane The flux characteristics of example compositions having two layers—a first active agent layer that includes a cross-linked acrylic acid polymer, and a skin adhesive layer—were evaluated. Two of compositions (Compositions 26 and 27) included an ethylene vinyl acetate/vinyl acetate membrane (CoTran™ 9726 membrane or CoTran™ 9707 membrane) disposed between the two layers. The specific makeup of these compositions is shown in Table 7 below.

TABLE 7

Figure 10:
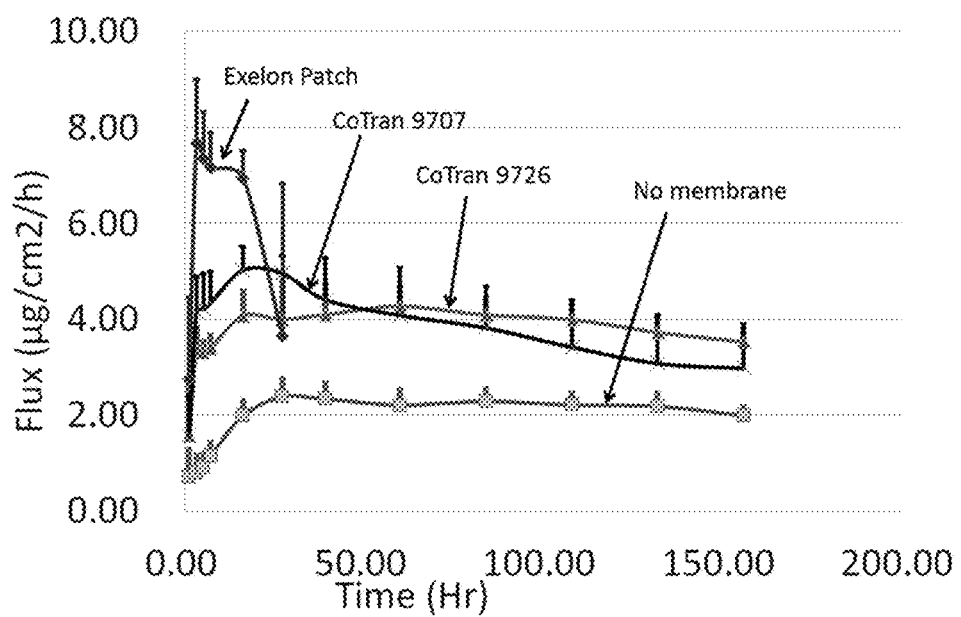
FIG. 10 shows a graph comparing the rivastigmine flux characteristics of membrane-containing and non-membrane-containing example transdermal compositions according to the present disclosure.
Figure 11A:
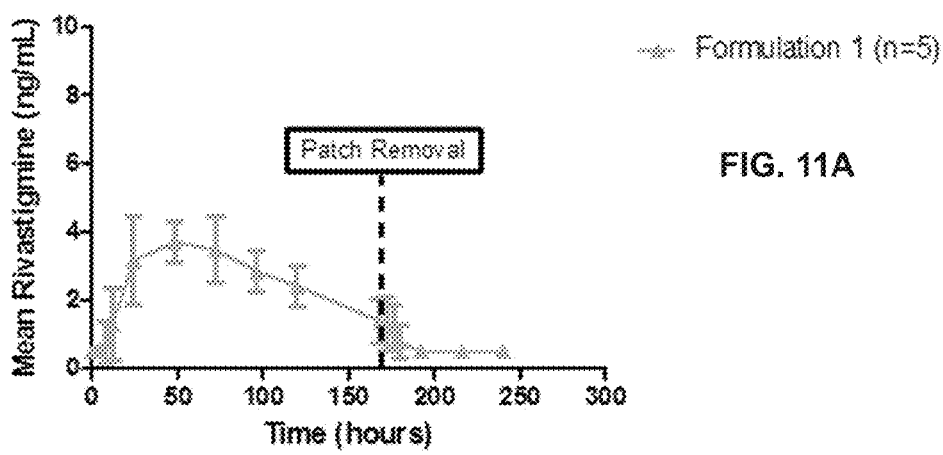
FIGS. 11A to 11D show graphs of results observed in a Mini-pig trial, as detailed in the Experimental Section, below.
Figure 11B:
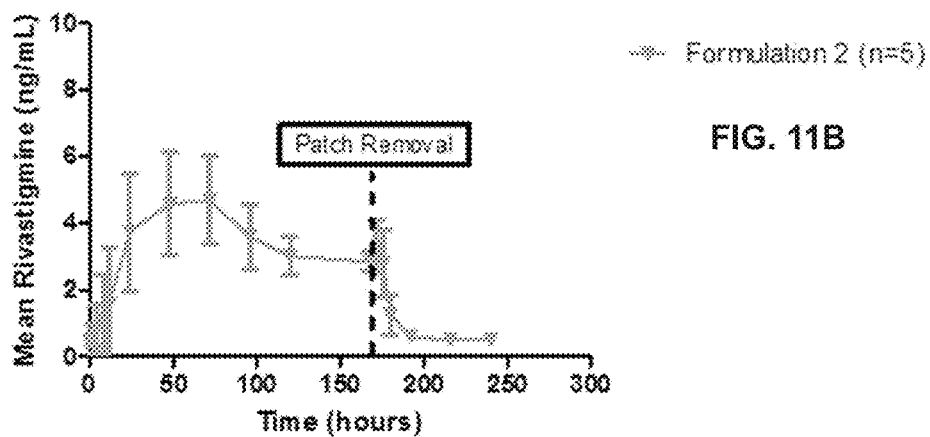
Figure 11C:
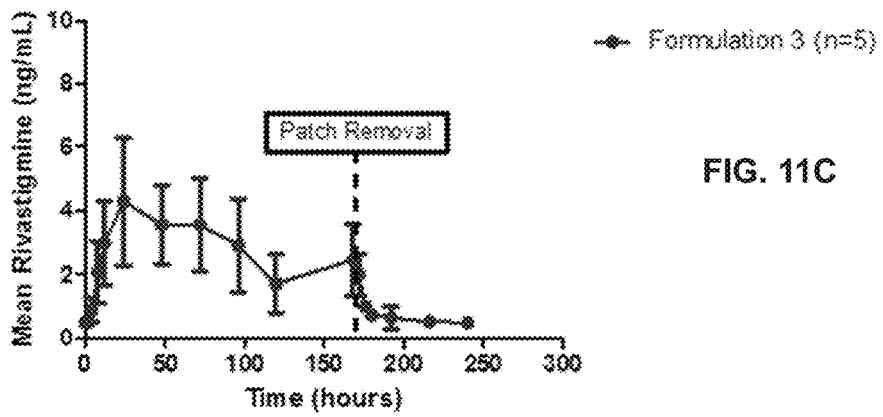
Figure 11D:
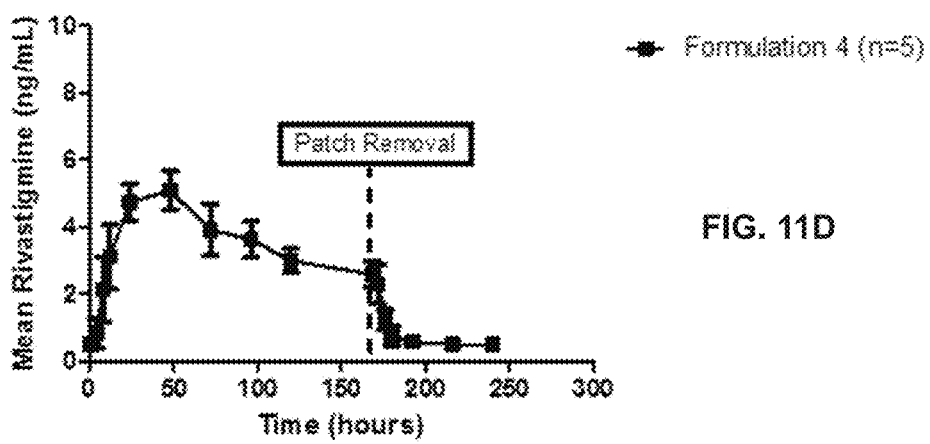

Ethylene Vinyl Acetate/Vinyl Acetate membrane compositions shown in FIG. 10

|  | Composition 25 | Composition 26 | Composition 27 |
|---|---|---|---|
| Active Agent Layer | 30% Rivastigmine<br>15% Plastoid<br>5% Carbopol 974P<br>49.9% Duro-Tak 2353<br>0.1% Vitamin E<br>24 mg/cm$^2$ coat weight | 30% Rivastigmine<br>15% Plastoid<br>5% Carbopol 974P<br>49.9% Duro-Tak 2353<br>0.1% Vitamin E<br>24 mg/cm$^2$ coat weight | 30% Rivastigmine<br>15% Plastoid<br>5% Carbopol 974P<br>49.9% Duro-Tak 2353<br>0.1% Vitamin E<br>24 mg/cm$^2$ coat weight |
| Membrane | None | CoTran 9726 | CoTran 9707 |
| Adhesive Layer | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight | 99.9% Duro-Tak 9301<br>0.1% Vitamin E<br>3 mg/cm$^2$ coat weight |

As shown in FIG. 10, compositions including an ethylene vinyl acetate/vinyl acetate membrane disposed between the active agent layer and the adhesive layer exhibited a sustained flux for 7 days, while the Exelon® patch exhibited a marked decrease in flux after day 1.

8. Minipig Study

A. Formulations Tested

Four different formulations were prepared, as summarized in Table 8, below.

TABLE 8

| Formulation | Formulation #1 | Formulation #2 | Formulation #3 | Formulation # 4 |
|---|---|---|---|---|
| Rivastigmine | 15 | 15 | 20 | 20 |
| Carbopol 974P | 0 | 0 | 2 | 2 |
| Vitamin E | 0.1 | 0.1 | 0.1 | 0.1 |
| Plastoid B | 10 | 10 | 10 | 10 |
| DT-2353 | 74.9 | 74.9 | 67.9 | 67.9 |
| Total wt % | 100 | 100 | 100 | 100 |
| Coat Weight (mg/cm$^2$) | 24 | 48 | 18 | 36 |

B. Protocol

Gottingen Mini-pigs approximately 6 months of age were used for the study (n=5 for each formulation). In the study, a test topical formulation was applied to the skin of the Mini-pig at the beginning of day 1 (t=0), and was removed at the end of day 7(t=168 hours). Total patch wear period was 168 hours. Blood sample collection time was at t=0, 0.5, 1, 2, 4, 8, 12, 24, 48, 72, 96, 120, 168, 172, 176, 180, 192, 216, 240 hours after the topical formulation application.

C. Results

The observed results are graphically illustrated in FIGS. 11A to 11D.

The Cmin/Cmax (=minimum plasma level of Rivastigmine over maximum, will represent the depletion) during the 7 days patch wearing period was observed. The results are provided in Table 9, below.

TABLE 9

|  | Cmax (ng/mL) | | Cmin (ng/mL) | | Cmin/Cmax |
|---|---|---|---|---|---|
|  | Average | STDEV | Average | STDEV |  |
| Formulation 1 | 4.22 | 0.48 | 1.40 | 0.65 | 0.33 |
| Formulation 2 | 4.90 | 1.48 | 2.68 | 0.38 | 0.55 |
| Formulation 3 | 4.94 | 1.26 | 1.38 | 0.49 | 0.28 |
| Formulation 4 | 5.16 | 0.56 | 2.59 | 0.40 | 0.50 |

It is noted that if Cmin/max is low, it means that the topical formulation is not retaining the drug administration during wear period, and blood concentration continues to decrease of the wear time of the topical formulation. In some instances, a ratio of 0.4 or more is selected for a desirable Cmin/Cmax value. Formulations 2 and 4 satisfy this criteria.

Figure 12:
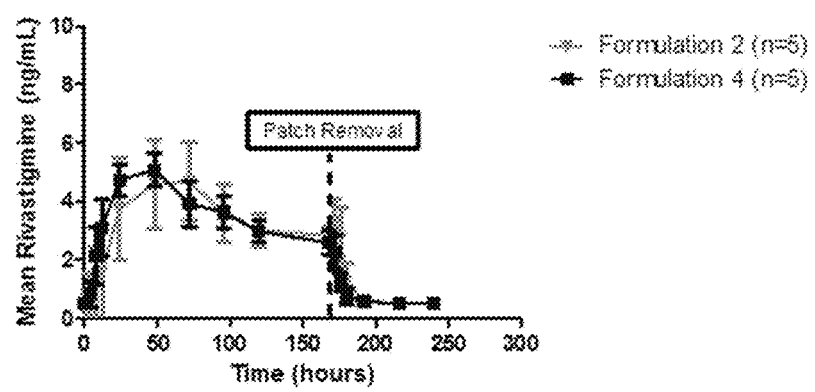
FIG. 12 shows a graph comparing the results observed with two topical formulations, one with and one without a carbomer, in a Mini-pig trial, as detailed in the Experimental Section, below.

The results observed with Formulations 2 and 4 and graphically illustrated and compared in FIG. 12. As can be seen from FIG. 12 and the Table 10, below, the PK profile for Formulations 2 and 4 is equivalent, while Formulation 4 with Carbomer (Carbopol 974P) is thinner (=easier to manufacture). Therefore, Formulation 4 is superior to Formulation 2.

TABLE 10

|  | Coat weight (mg/cm2) | AUC(0-240) (ng/mL*h) | Cmax (ng/mL) | Cmin (ng/mL) |
|---|---|---|---|---|
| Formulation 2 | 48 | 643.3 ± 140.2 | 4.9 ± 1.5 | 2.68 ± 0.38 |
| Formulation 4 | 36 | 648.8 ± 70.8 | 5.2 ± 0.6 | 2.59 ± 0.40 |
| Ratio (Form4/Form2) | 0.75 | 1.01 | 1.06 | 0.97 |

Although the foregoing describes the present disclosure in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims.

Accordingly, the preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A transdermal composition, the composition comprising:
    an active agent layer comprising rivastigmine and a solubility modulator comprising a crosslinked acrylic acid homopolymer;
    a backing; and
    an adhesive layer disposed on a side of the active agent layer opposite the backing.

2. The composition according to claim 1, wherein the rivastigmine is present in an amount of from 10% w/w to 75% w/w.

3. The composition according to claim 1, wherein the active agent layer comprises a pressure-sensitive adhesive.

4. The composition according to claim 3, wherein the pressure-sensitive adhesive is present in an amount ranging from 5% to 90%.

5. The composition according to claim 3, wherein the pressure-sensitive adhesive is an acrylate copolymer.

6. The composition according to claim 1, wherein the active agent layer comprises an antioxidant.

7. The composition according to claim 1, wherein the coat weight of the active agent layer ranges from 10 mg/cm$^2$ to 90 mg/cm$^2$.

8. The composition according to claim 1, wherein the active agent layer has a surface area ranging from 15 cm$^2$ to 60 cm$^2$.

9. The composition according to claim 1, wherein the adhesive layer comprises a pressure-sensitive adhesive.

10. The composition according to claim 9, wherein the adhesive layer comprises a pressure-sensitive adhesive present in an amount of from 75% to 100%.

11. The composition claim 9, wherein the adhesive layer comprises an acrylate copolymer pressure-sensitive adhesive.

12. The composition claim 9, wherein the pressure-sensitive adhesive of the adhesive layer is a silicone adhesive.

13. The composition claim 9, wherein the pressure-sensitive adhesive of the adhesive layer comprises polyisobutene.

14. The composition claim 1, wherein the adhesive layer comprises an antioxidant.

15. The composition according to claim 1, wherein the coat weight of the adhesive layer is from 2 mg/cm$^2$ to 5 mg/cm$^2$.

16. The composition according to claim 1, wherein the composition comprises a membrane disposed between the active agent layer and the adhesive layer.

17. The composition according to claim 1, wherein the composition comprises a release liner.

18. A method comprising:
    applying to a skin site of a subject a transdermal composition according to claim 1 in a manner sufficient to achieve a therapeutic flux of the rivastigmine for 24 hours or longer.

19. The method according to claim 18, wherein the subject is suffering from dementia.

20. A kit comprising two or more transdermal compositions according to claim 1.

21. The composition according to claim 1, wherein the solubility modulator is selected from the group consisting of a crosslinked acrylic acid homopolymer crosslinked with an allyl ether of sucrose, a crosslinked acrylic acid homopolymer crosslinked with an allyl ether of pentaerythritol and a crosslinked acrylic acid homopolymer crosslinked with divinyl glycol.

22. The composition according to claim 1, wherein the solubility modulator is present in an amount sufficient to reduce the transdermal delivery of rivastigmine from the active agent layer.

23. The composition according to claim 1, wherein the solubility modulator is a solubility enhancer.

* * * * *

UNITED STATES PATENT AND TRADEMARK OFFICE
CERTIFICATE OF CORRECTION

PATENT NO.        : 10,357,463 B2
APPLICATION NO.   : 15/917478
DATED             : July 23, 2019
INVENTOR(S)       : Kensuke Murata Page 1 of 1

It is certified that error appears in the above-identified patent and that said Letters Patent is hereby corrected as shown below:

In the Specification

Replace "Colran™" with -- CoTran™ -- Column 14, Lines 52 and 53.

Signed and Sealed this
Twenty-eighth Day of January, 2020

Andrei Iancu
*Director of the United States Patent and Trademark Office*